United States Patent [19]
Ono

[11] Patent Number: 5,222,497
[45] Date of Patent: Jun. 29, 1993

[54] HOLLOW NEEDLE FOR USE IN MEASUREMENT OF VISCOSITY OF LIQUID

[75] Inventor: Yonezo Ono, Tatebayashi, Japan

[73] Assignee: Nissho Corporation, Osaka, Japan

[21] Appl. No.: 824,293

[22] Filed: Jan. 23, 1992

[30] Foreign Application Priority Data

Jan. 25, 1991 [JP] Japan ................................. 3-25746

[51] Int. Cl.$^5$ .............................................. A61B 5/00
[52] U.S. Cl. .................................... 128/637; 604/272; 73/54.09
[58] Field of Search ............... 128/672, 673, 748, 763, 128/764; 73/54.01, 54.04, 54.07, 54.09

[56] References Cited

U.S. PATENT DOCUMENTS 2,840,069  6/1958  Squire et al. ......................... 604/272
3,893,451  6/1975  Durand et al. ....................... 128/673
4,083,363  4/1978  Philpot, Jr. ......................... 73/54.07
4,431,009  2/1984  Harino et al. ....................... 128/673

Primary Examiner—Lee S. Cohen
Assistant Examiner—Marianne Harley
Attorney, Agent, or Firm—Birch, Stewart, Kolasch & Birch

[57] ABSTRACT

A hollow needle for use in measurement of viscosity of liquids, includes at least one small and slender straight tube and a hub fixed thereto and provided with a connector member. The tube includes a piercing portion and a suction portion extending therefrom to form an opening for suction of a liquid to be measured. The piercing portion has a sharp edge at its one end and is fixed to the hub at the other end, the inside diameter (D) of a bore of the tube including the edge of the piercing portion being made uniform over a specified length (L) of the tube defined by equation: L/D=50 to 500.

19 Claims, 3 Drawing Sheets

HOLLOW NEEDLE FOR USE IN MEASUREMENT OF VISCOSITY OF LIQUID

BACKGROUND OF THE INVENTION

1. Field of the Invention

The present invention relates to a hollow needle for use in measurement of viscosity of liquids and, more particularly, a hollow needle for use in a device for measurement of viscosity of liquids which is easy to operate and makes it possible to measure the viscosity of a liquid in a very short time.

2. Description of the Prior Art

As is well-known, health conditions of a person have great influences on the viscosity of blood. In fact, the viscosity of blood of a person suffering from anemia, chronic renal insufficiency requiring hemodialysis, myocardial infarction, diabetes mellitus or malignant tumor, differs greatly from that of a person in normal health. In advanced nations, adult diseases such as, for example, myocardial infarction, thrombo-embolism and diabetes mellitus are increasing rapidly with increase in aged population. Thus, it can be said measurement of the viscosity of the blood is an important and effective factor essential for therapy and/or prevention of diseases.

So far, various devices have been developed to measure the viscosity of liquids or solutions. In the sphere of clinical medicine, however, there have been employed two devices, i.e., a capillary viscometer and a rotation viscometer. In the former, the viscosity of a liquid is measured by introducing the liquid into the capillary viscometer, and then causing the liquid to flow under external forces such as the gravitational force through a capillary or a fine tube of uniform bore to obtain the time required for its meniscus to pass through between predetermined levels. Such a capillary viscometer has been used widely to measure the viscosity of blood plasma. However, it is rarely the case that the capillary viscometers are applied to measure the viscosity of blood as the natural blood is non-Newtonian in its flow characteristics.

In order to determine the intrinsic viscosity, it is required to measure the viscosity several times using the same liquid and capillaries of varying diameter.

The measurement of the viscosity of bloods has generally been carried out with the rotation viscometers. A typical rotation viscometer comprises two concentric cylinders, the inner or outer cylinder being rotated in or rotated around the fixed outer or inner cylinder. In such a viscometer, the liquid is placed between two cylinders and either of the cylinders is rotated around its axis to measure its torque.

However, the rotation viscometers have the following disadvantages: (a) several measurements must be made on the same blood at different shear stresses in order to determine the intrinsic viscosity; (b) calculations are troublesome and lead to noticeable errors as they require graphical differentiation of logarithmic values by logarithmic values; (c) special and unstable flows such as Taylor vortex take place at high rotating rates; (d) the liquid to be examined generates heat by its viscosity; (e) there is a fear of causing deflection of blood corpuscles because of the centrifugal force; (f) the measurement for each specimen takes a long time; and (g) the viscometer is troublesome to handle as the viscometer must be cleaned every measurement by washing it with water and then drying the same to remove the blood adhered thereto.

To solve these problems, various new methods employing a roller pump system or a hollow fiber module have been proposed for measurement of the viscosity of blood. However, none of the viscometers of the prior art satisfies all the conditions required for application to the clinical medicine.

As is known, the blood is non-Newtonian in its flow characteristics, whereas the blood plasma behaves Newtonian. It is said, therefore, that the non-Newtonian behaviors of the blood result from the presence of blood corpuscles floating within the plasma. In particular, it is said that factors which have influences on the flow characteristics of the blood are the orientation of blood corpuscles and their various shapes such as disc shapes with concave surfaces, streamlined shapes or projectile shapes. The effect of such factors on the flow characteristics varies with a period of time elapsed from the blood collecting, and is affected by addition of other substances such as, for example, anticoagulants to the blood. Thus, it can be said that the best way to determine the flow characteristics of blood including its non-Newtonian behaviors is to select the blood circulating in the blood vessels of the body as the object of measurement.

However, there is no viscometer which makes it possible to directly measure the flow characteristics of the blood circulating in the blood vessels of the body. Thus, it is inevitable to use the collected blood as the object of measurement. In such a case, it is required to measure the flow characteristics of the blood correctly in the least time possible after blood-collecting, as well as to collect the blood without incorporating any other materials such as anticoagulants into the freshly drawn blood.

In addition, in order to adapt rheological blood tests to a routine clinical medicine, it is required to satisfy the following three conditions: (a) the measurement can be made with the natural blood; (b) the measurement can be made instantly at the bed side; and (c) the viscometer is easy to operate and operable for any person.

To solve these problems, it has been proposed in Japanese patent application No. Heisei 2-418855 to use a device for measurement of viscosity of liquid, comprising an evacuated vessel composed of a hollow cylinder and a pair of stoppers provided at both ends of the cylinder to keep a lowered pressure of the vessel, a hollow needle adapted to be pierced into one of the stoppers to let it go into the vessel, a pressure sensor for detecting an internal pressure of the vessel, a connecting needle pierced into the other stopper to communicate the pressure sensor with the interior of the vessel, and a means for calculating the viscosity of a liquid from change of the internal pressure of the vessel. This device is easy to operate and makes it possible to correctly and rapidly measure the viscosity of a liquid with a small amount of the liquid.

In such a device, the liquid to be measured in the liquid container is introduced into the vessel through the hollow needle by the difference between the internal pressure of the evacuated vessel and the atmospheric pressure acting on the surface of the liquid in the container. In order to put such a device into practical use, it is required to develop an inexpensive hollow needle which can be mass produced with ease.

SUMMARY OF THE INVENTION

It is therefore an object of the present invention to provide a hollow needle for use in a device for measurement of a viscosity of liquid of the kind wherein a liquid to be measured in a liquid container is forced to flow into an evacuated vessel through the hollow needle by the difference between an internal pressure of the evacuated vessel and the atmospheric pressure acting on the surface of the liquid in the liquid container.

The above and other objects of the present invention are achieved by providing a hollow needle for use in measurement of viscosity of liquids, comprising at least one small and slender tube and a hub attached thereto and provided in its surface with a connecting means, said tube including a piercing portion and a suction portion extending therefrom to form an opening for suction of a liquid to be measured, said piercing portion having a sharp edge at its one end and being fixed to said hub at the other end, the inside diameter (D) of a bore of said tube including the edge of the piercing portion being made uniform over a specified length (L) of the tube defined by equation: $L/D = 50$ to $500$.

The above and other objects, features and advantages of the present invention will be fully understood from the following description with reference to the accompanying drawings, which show, by way of example only, preferred embodiments thereof.

DETAILED EXPLANATION OF THE PREFERRED EMBODIMENT

Figure 1:
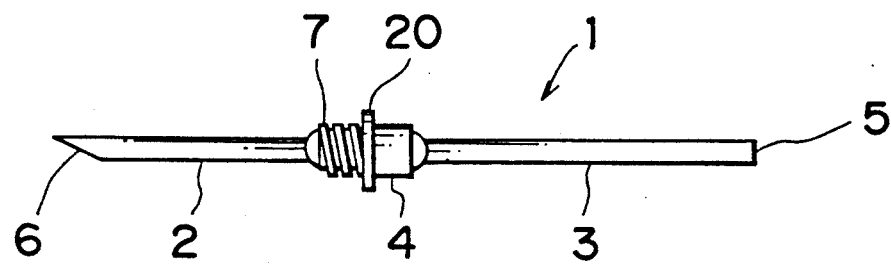
FIG. 1 is a plan view of a hollow needle showing one embodiment of the present invention.
Figure 2:
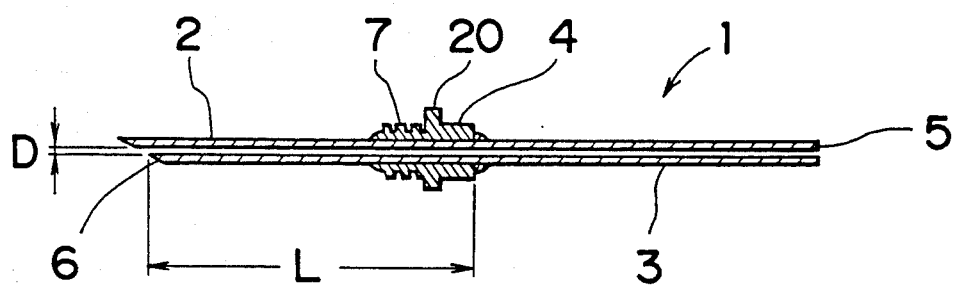
FIG. 2 is a section view of a hollow needle of FIG. 1, taken along a line passing through its axis.

Referring now to FIGS. 1 and 2, there is shown a hollow needle 1 of the present invention, which comprises a small and slender straight tube including two parts, i.e., a piercing portion 2 and a suction portion 3, and a hub 4 provided in its outer surface with a thread 7 serving as a connecting means.

The piercing portion 2 has a sharp edge 6 at its one end and its other end is inserted into a bore of the hub 4 and fixed thereto by a bonding agent. The piercing portion 2 is generally made of a metal or a relatively rigid synthetic resin. The typical metal is stainless steels (e.g., SUS 304 defined by JIS). Typical rigid synthetic resin includes, without being limited to, polypropylenes, ABS resins, rigid polyvinyl chlorides and polycarbonates.

The inside diameter (D) of the bore of the piercing portion 2 including its edge, or that of the bore of both the piercing portion 2 and the suction portion 3, is made uniform over a specified length (L) of the tube defined by equation, $L/D = 50$ to $500$. The most preferred value of L/D is of the order of 150. The reasons why the ratio of L to D, i.e., L/D has been limited to the value ranging from 50 to 500 are as follows. If the value of L/d is less than 50, the flow rate of the liquid shows a variation resulting from influences of shapes of the suction portion 3 with a different diameter, a vessel or a container mentioned below, thus making it impossible to measure the viscosity of liquid. If the value of L/D exceeds 500, pressure loss becomes large and the flow of the liquid of a high viscosity does not occur.

In general, the inside diameter (D) of the piercing portion 2 ranges from 0.2 to 2.5 mm. Because, if the diameter (D) is less than 0.2 mm, the flow resistance becomes considerably large and the flow of the liquid does not occur. If the diameter (D) of the bore exceeds 2.5 mm, it is difficult to pierce the needle into a stopper without causing increase in the internal pressure of an evacuated vessel mentioned below.

Figure 3:
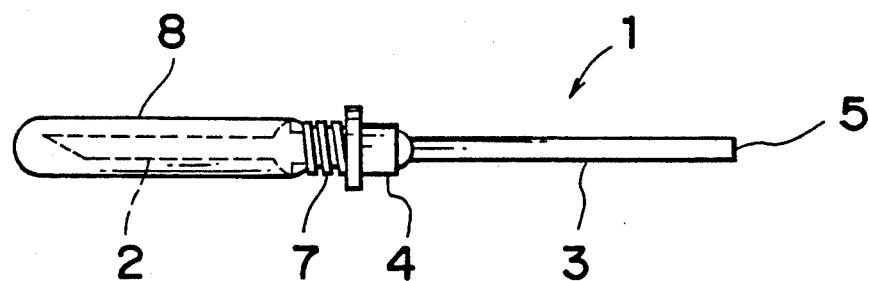
FIG. 3 is a side view of a hollow needle showing another embodiment of the present invention.

As shown in FIG. 3, the piercing portion 2 may be covered with a cap 8 of rubber to protect its sharp edge 6 or to prevent it from contamination with bacteria. This makes it possible to draw the blood directly from the body.

Figure 5:
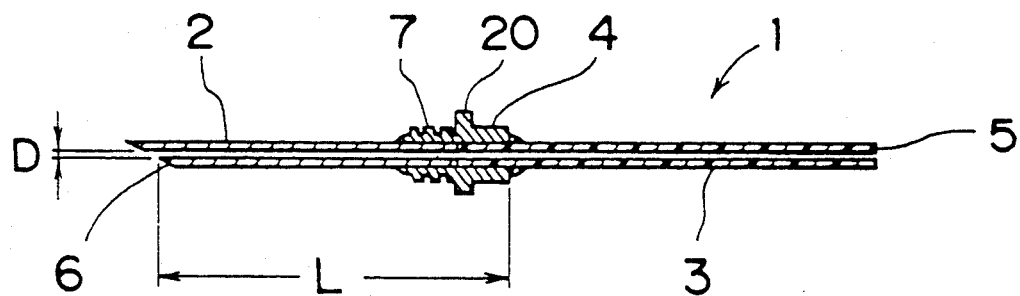
FIG. 5 is a section view of a hollow needle with a suction portion formed separately from a piercing portion.

The suction portion 3 has an opening for suction of a liquid to be measured and is generally formed as an integral part of the piercing portion 2. However, the suction portion 3 may be formed as a separate member as occasion demands as shown in FIG. 5. In this case, the suction portion 3 is connected to the piercing portion 2 by the hub 4 or to the hub 4 by a suitable connecter (not shown). If the suction portion 3 is an integral part of the piercing portion 2, it is made of the same material as that of the piercing portion 2, i.e., metals such as stainless steel or relatively rigid synthetic resins such as polypropylenes, ABS resins, rigid polyvinyl chlorides, polycarbonates, etc. However, if the suction portion 3 is a small and slender tube formed separately from the piercing portion 2, there may be made of a non-rigid synthetic resin such as polyethylenes and non-rigid polyvinyl chlorides.

Figure 6:
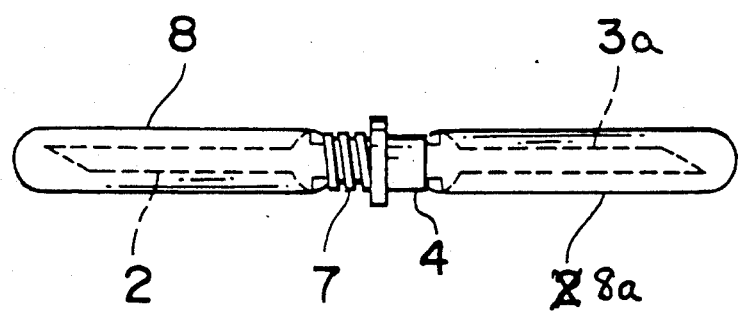
FIG. 6 is a side view of still another embodiment of the present invention.

The suction portion 3 generally has no sharp edge, but it may have a sharp edge 3a similar to that of the piercing portion 2 as occasion demands and as shown in FIG. 6. If the suction portion of the needle is used as a blood-collecting tip to directly draw blood from the body, it is required to protect the sharp edge of the suction portion 3 with a suitable cap 8a to prevent it from damage, as well as to draw blood in a sterile condition.

Figure 4:
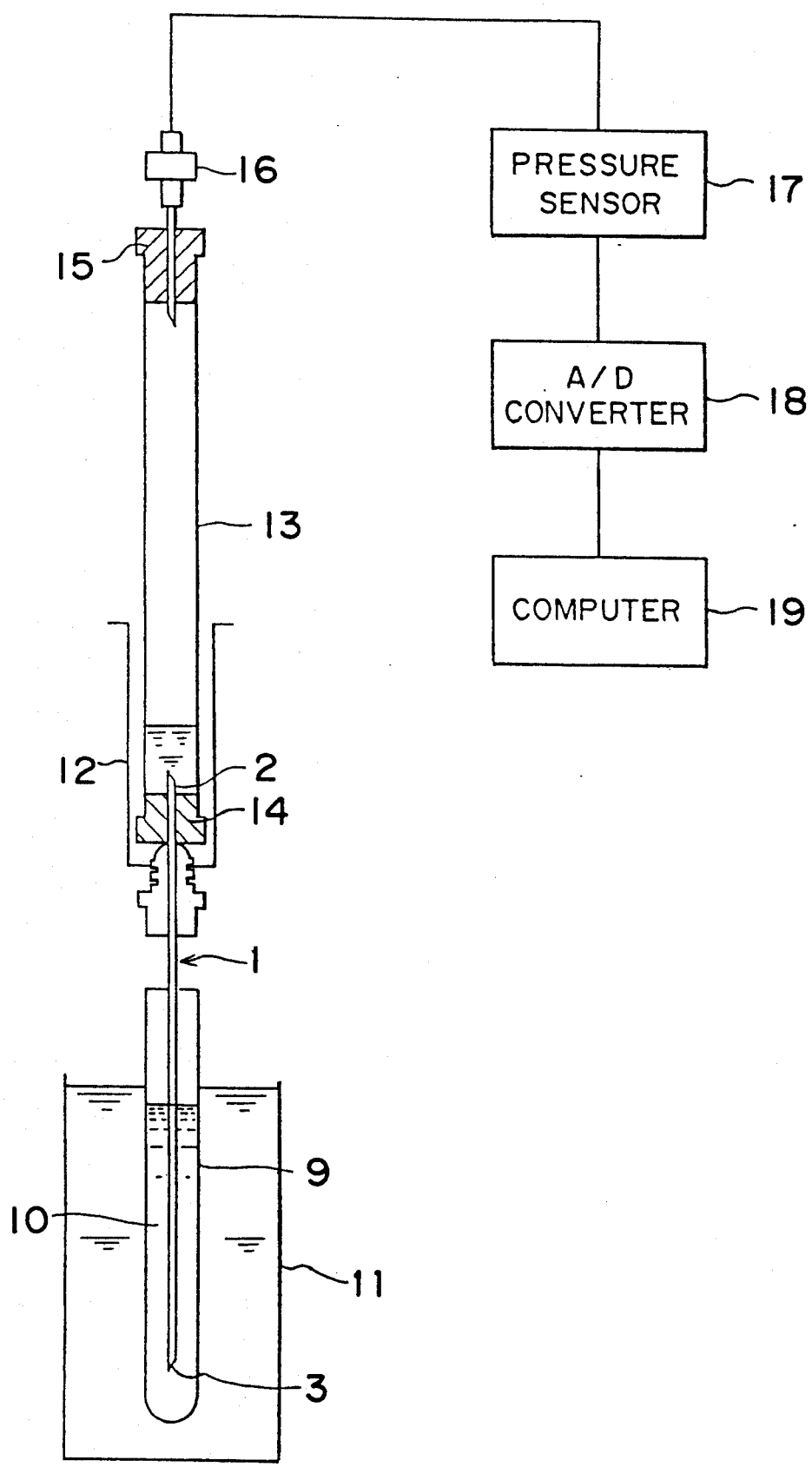
FIG. 4 is a schematic diagram of a device for measurement of viscosity of liquids, including the hollow needle of FIG. 1.

The hub 4 is a portion for fixing the needle 1 to a holder 12 shown in FIG. 4 and is provided on the side of the piercing portion 2 with a thread 7 serving as a connecting means. As a connecting means, there may be used those such as Luer-Loc, press-fitting and the like. The hub 4 is also provided with a flange 20 to limit the movement of the needle in the direction of the piercing portion 2 when fixing the needle 1 to the holder 12. However, it is necessarily required to provide the flange 20 on the hub 4. As a material for the hub, there may be used those such as polypropylenes, rigid polyvinyl chlorides, ABS resins and polycarbonates.

The above hollow needle 1 is used as a part of a device for measurement of viscosity of liquids, or, a viscometer mentioned below.

Referring now to FIG. 4, there is shown a device for measurement of viscosity of liquid, comprising a liquid container 9 for storing a liquid 10 to be measured, a thermostat 11, the hollow needle 1, a holder 12, an evacuated vessel 13, a connecting needle 16, a pressure sensor 17 for detecting an internal pressure of the vessel, an A/D convertor 18, and a computer system 19 for calculating viscosity of the liquid.

The evacuated vessel 13, i.e., a small closed vessel in which the gas pressure is less than normal, is generally composed of a hollow cylinder and a pair of sealing members 14, 15 of a gummy elastic material fitted in its both openings. The gas pressure of the evacuated vessel 13 has been lowered to a certain predetermined pressure, generally, of the order of −180 mmHg expressed in a value relative to atmospheric pressure. Thus, the liquid 10 in the container 9 is introduced into the vessel 13 through the hollow needle 1 by piercing the hollow needle 1 into the sealing member 14 of the vessel 13. The connecting needle 16 is pierced into the sealing member 15 on the opposite side of the vessel 13 to transfer its internal pressure to the pressure sensor 17. The holder 12 is composed of a short hollow cylinder closed at one end and so designed as to fix the hollow needle 1 in position as well as to properly guide the same to a central portion of the sealing member 14 of the vessel 13.

In use, the evacuated vessel 13 is immovably fixed by a suitable holding device (not shown) and then the connecting needle 16 is pierced into the sealing member 15 until its lower end extends into the interior of the vessel 13, as shown in FIG. 4.

After or before the above operation, the liquid container 9 containing the liquid 10 to be measured is placed in the thermostat 11 maintained at a test temperature, and then allowed to stand for a certain period to keep the temperature of the liquid constant, while dipping the suction portion 3 of the needle 1 into the liquid 10 contained in the container 9.

After making the computer 19 ready to work, the edge 6 of the hollow needle 1 is pierced into the sealing member 14 of the vessel. As soon as the piercing portion 2 enters into the interior of the vessel 13, the liquid 10 in the container 9 is forced to flow into the vessel 13 through the needle 1 by the difference between the internal pressure of the vessel 13 and the pressure acting on the surface of the liquid 10 in the container 9, actually, the atmospheric pressure.

With increase of the inflow of the liquid 10, the volume of the uncharged space of the vessel 13 decreases, while the internal pressure of the vessel 13 increases gradually. The inflow of the liquid continues until the internal pressure of the vessel 13 reaches the atmospheric pressure.

During the inflow of the liquid, changes of the internal pressure of the vessel 13 are detected and transformed into electric signals by the pressure sensor 17, and the electric signals are then converted to digital signals by the A/D converter 18. The output signals of the A/D converter 18 are taken in by the computer 19 through its I/0 ports (not shown) at a certain interval of time to determine changes of the internal pressure of the vessel 13. The pressure changes are converted to the volume change of the uncharged space of the vessel 13 on the basis of Boyle's law.

The change rate of the internal pressure of the vessel 13 for a given period of time depends on the flow rate of the liquid 10 running through the hollow needle 1, and the flow rate of the liquid varies with the viscosity of the liquid. Thus, the viscosity of the liquid can be determined by detecting the change of the internal pressure of the vessel 13. Since the coefficient of viscosity of the liquid flowing in the steady state is defined as a ratio of the shear stress to the apparent shear rate at a point on the wall of the needle 1, and since the shear stress and the apparent shear rate are respectively related to the change of the internal pressure of the vessel 13 and the flow rate of the liquid, the coefficient of the viscosity can be determined by calculating the shear stress and the apparent shear rate from the pressure change of the vessel 13 and the volume change of the uncharged space of the vessel 13, using equations theoretically derived according to the flow model of the liquid. These calculations are carried out by the computer system 19 in accordance with the programmed steps, but procedures for determination of the viscosity of liquid are omitted from the explanation as they are not the subject matter of the present invention.

As will be understood from the above, the use of the hollow needle of the present invention as a part of the device for measurement of viscosity of liquids provides the following advantages.

(a) The efficiency of measurement can be considerably improved and the device for measurement of viscosity of liquid employing the hollow needle of the present invention is effective for the measurement of the viscosity of blood which is required to complete the measurement within about 10 minutes after blood-collecting. Because, in case of the viscometers of the prior art, it is required for the same liquid to measure the viscosity of liquid several times at various pressure differences to determine the intrinsic viscosity. In contrast therewith, in case of the device for measurement of the viscosity of liquid employing the hollow needle of the present invention, there is no need to repeat the measurement of the viscosity of liquid since the viscosity of liquid is determined by detecting the internal pressure of the vessel, which changes continuously with time, to determine the pressure difference between the internal pressure of the vessel and atmospheric pressure, and then continuously calculating the corresponding flow rates of liquid on the basis of Boyle's Law, thus making it possible to determine the viscosity of blood in a time of the order of 1 or 2 minutes, using a small amount of the liquid of the order of 5 to 8 ml.

(b) Since the hollow needle is inexpensive and can be discarded after every use, there is no need to wash the needle as well as other parts of the device for measurement of viscosity of liquids.

(c) Since the hollow needle of the present invention is simple in construction, it is possible to produce the hollow needle at a low price.

(d) The hollow needle of the present invention makes it possible to carry out the measurement of the viscosity of liquid with ease only by piercing the hollow needle into the sealing member of the evacuated vessel.

(e) It is possible to handle any liquids poisonous to human as the liquid to be measured is never brought into contact with the body.

What is claimed is:

1. A hollow needle for use in measurement of viscosity of liquids, comprising:
   at least one small slender tube having a piercing portion at a first end thereof and a suction at an opposing second end thereof;
   a hub member surrounding an outer peripheral surface of said tube at a substantially central portion thereof, said hub member including an external threaded connector area at an end of said hub member adjacent to the piercing portion of said tube;

a sharp piercing edge provided on a distal end of the piercing portion of said tube;

a bore formed in said tube over an axial length thereof, said bore having a uniform inside diameter (D) over a specified length (L) of said tube defined by an equation: $L/D = 50$ to $500$.

2. The hollow needle according to claim 1, wherein the inside diameter (D) of the bore ranges from 0.2 to 2.5 mm.

3. The hollow needle according to claim 1, wherein the piercing portion of said tube is covered with a cap of a gummy elastic material.

4. The hollow needle according to claim 1, wherein the piercing portion and the suction portion are formed integrally with one another.

5. The hollow needle according to claim 1, wherein the suction portion is a small and slender tube formed separately from the piercing portion and connected thereto by said hub member.

6. The hollow needle according to claim 1, wherein said hub is connected to said tube by a bonding agent.

7. The hollow needle according to claim 1, wherein said piercing portion is formed of a metal.

8. The hollow needle according to claim 7, wherein said metal is stainless steel.

9. The hollow needle according to claim 1, wherein said piercing portion is formed of a relatively rigid synthetic resin.

10. The hollow needle according to claim 9, wherein said synthetic resin includes at least one of polypropylene, ABS resin, rigid polyvinyl chloride and polycarbonate.

11. The hollow needle according to claim 1, wherein a preferred value of L/D is 150.

12. The hollow needle according to claim 1, wherein said suction portion is formed of a metal.

13. The hollow needle according to claim 12, wherein said metal is stainless steel.

14. The hollow needle according to claim 1, wherein suction portion is formed of a relatively rigid synthetic resin.

15. The hollow needle according to claim 14, wherein relatively rigid synthetic resin includes at least one of polypropylene, ABS resin, rigid polyvinyl chloride and polycarbonate.

16. The hollow needle according to claim 1, wherein said suction portion is formed of a non-rigid synthetic resin.

17. The hollow needle according to claim 16, wherein said non-rigid synthetic resin is at least one of polyethylene and non-rigid polyvinyl chloride.

18. The hollow needle according to claim 1, wherein said hub includes a flange for limiting movement of said tube in the direction of the piercing portion.

19. The hollow needle according to claim 1, wherein said hub is formed of at least one of polypropylene, rigid polyvinyl chloride, ABS resin and polycarbonate.

* * * * *